United States Patent
Khurgin et al.

(10) Patent No.: US 8,348,838 B1
(45) Date of Patent: Jan. 8, 2013

(54) SURGICAL SUCTION INSTRUMENT PROVIDING ILLUMINATION

(76) Inventors: Boris Khurgin, New York, NY (US); Jacob Leon Khurgin, Philadelphia, PA (US)

( * ) Notice: Subject to any disclaimer, the term of this patent is extended or adjusted under 35 U.S.C. 154(b) by 0 days.

(21) Appl. No.: 13/134,748

(22) Filed: Jun. 16, 2011

(51) Int. Cl.
*A61B 1/06* (2006.01)

(52) U.S. Cl. .................. 600/249; 600/212; 600/245

(58) Field of Classification Search .............. 600/212, 600/235, 245, 249
See application file for complete search history.

(56) References Cited

U.S. PATENT DOCUMENTS

| | | | |
|---|---|---|---|
| 4,648,838 A * | 3/1987 | Schlachter | 433/29 |
| 5,683,350 A * | 11/1997 | Paul et al. | 600/249 |
| 6,569,089 B1 | 5/2003 | Covington et al. | |
| 6,776,756 B2 | 8/2004 | Feldon et al. | |
| 2003/0109854 A1 | 6/2003 | Chen | |
| 2008/0188727 A1 | 8/2008 | Benaron et al. | |
| 2009/0036744 A1 * | 2/2009 | Vayser | 600/182 |
| 2009/0192503 A1 | 7/2009 | Epshtein et al. | |
| 2009/0221991 A1 | 9/2009 | Lieponis | |
| 2009/0318798 A1 | 12/2009 | Singh et al. | |
| 2010/0056988 A1 | 4/2010 | Nishtala | |

* cited by examiner

*Primary Examiner* — Andrew Yang
*Assistant Examiner* — Olivia C Chang
(74) *Attorney, Agent, or Firm* — David L. Banner

(57) ABSTRACT

A surgical suction instrument having multiple LEDs for selectively providing illumination as light of different wavelengths at the tip thereof. Typically, at least one of the LEDs is chosen to emit polychromatic white light. Individual switches operable by either the surgeon or another member of the surgical team allow any combination of the LEDs to be energized, thereby creating numerous combinations of light wavelength from the novel surgical suction instrument. Control of the intensity of one or more of the LEDs may be provided to further determine the character of the composite light emitted from the multiple LEDs. The LEDs may be powered by self-contained batteries or from an external power source. The device may either be a single use, disposable device or, in alternate embodiments, may be a device intended for multiple uses and capable of withstanding sterilization.

10 Claims, 4 Drawing Sheets

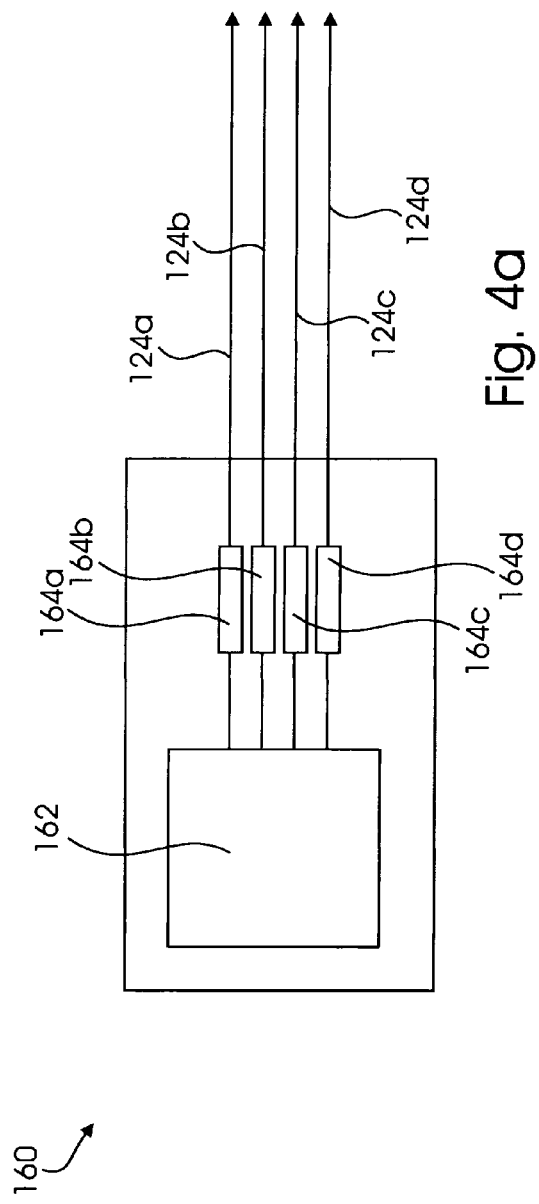
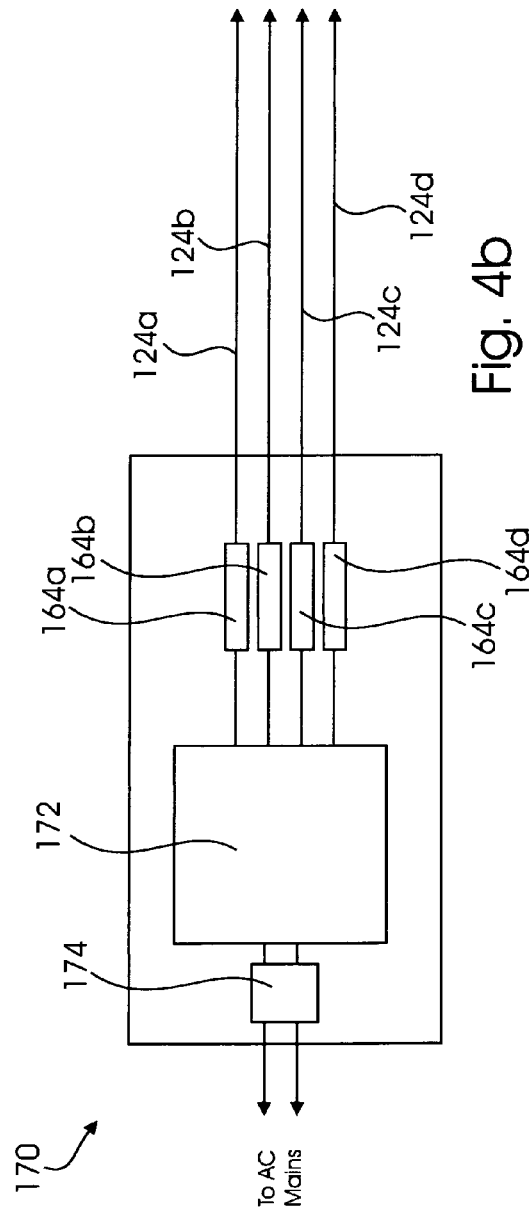

SURGICAL SUCTION INSTRUMENT PROVIDING ILLUMINATION

FIELD OF THE INVENTION

The invention pertains to surgical suction devices and, more particularly, to a suction instrument having a built-in light source.

BACKGROUND OF THE INVENTION

Modern surgical practice relies on proper visualization in the operating room. Retractors, overhead lights, suctioning devices and multiple other devices along with surgical assistants have been employed to aid the surgeon to adequately visualize a surgical site. Despite this, the problem of inadequate lighting often persists. This is especially true when the surgical site is shadowed or occluded, such as when working deep within body cavities. Further, general illumination from typical overhead surgical lighting systems is typically a broad spectrum light. Under some circumstances, illumination having a particular wavelength supplied locally at the surgical site may be helpful in allowing the surgeon to differentiate a particular tissue type from a different tissue type or other anatomical feature.

A solution to the problem of inadequate lighting could ideally ease intraoperative frustration by the surgical team and ultimately improve postoperative outcomes.

A device to provide two of the most effective visualization aids, suctioning and lighting, has yet to be effectively embodied in a single, functional surgical tool. However, the advantages of effectively providing a suction instrument with a light sources are numerous.

DISCUSSION OF THE RELATED ART

Several attempts to combine a surgical instrument or other similar device with a light source may be found in the prior art. For example, United States Published Patent Application No. 2009/0221991 for MULTI-PURPOSE SURGICAL INSTRUMENT WITH REMOVABLE COMPONENT, published Sep. 3, 2009 upon application by Jonas V. Lieponis shows an aspiration conduit having a detachable tip and top illumination provided via optical fibers.

U.S. Pat. No. 6,776,756 for APPLANATION TONOMETER, issued Aug. 17, 2004 to Steven E. Feldon et al. discloses an applanation tonometer having a disposable tip and a light source.

United States Published Patent Application No. 2009/0318798 for FLEXIBLE VISUALLY DIRECTED MEDICAL INTUBATION INSTRUMENT AND METHOD, published Dec. 24, 2009 upon application by Errol Singh et al. shows a disposable medical intubation instrument having an illumination cable.

United States Published Patent Application No. 2010/0056988 for DRAINS FOR USE IN MEDICAL APPLICATIONS AND METHODS OF USING THE SAME, published Mar. 4, 2010 upon application by Vasu Nishtala shows a multi-passage drain conduit with a light source.

U.S. Pat. No. 6,569,089 for LIGHTED INTUBATING LARYNGOSCOPE, issued May 27, 2003 to Roy Covington et al. teaches a laryngoscope which may have light provided to a suction tip.

United States Published Patent Application No. 2008/0188727 for BROADBAND SOLID-STATE SPECTROSCOPY ILLUMINATOR AND METHOD, published Aug. 7, 2008 upon application by David A. Benaron et al. contemplates integration of illumination into the tip of a medical probe.

United States Published Patent Application No. 2009/0192503 for DEVICE, APPARATUS, AND METHOD OF ADIPOSE TISSUE TREATMENT, published Jul. 30, 2009 upon application by Halm Epshtein et al. shows a disposable needle for liposuction, having a light conducting body.

United States Published Patent Application No. 2003/0109854 for NASAL CLEANER, published Jun. 12, 2003 upon application by Chien-Li Chen shows a nasal cleaner having a suction tip and a lighting unit.

None of the patents and published patent applications, taken singly, or in any combination are seen to teach or suggest the novel surgical suction instrument providing illumination of the present invention.

SUMMARY OF THE INVENTION

In accordance with the present invention there is provided a surgical suction instrument providing illumination at the tip thereof. Multiple light emitting diodes (LEDs) selectively provide light at different wavelengths to facilitate differentiation of tissue types from one another. Typically, at least one of the LEDs is chosen to emit polychromatic white light. Individual switches operable by either the surgeon or another member of the surgical team allow any combination of the LEDs to be energized, thereby creating numerous combinations of light wavelength from the novel surgical suction instrument. In still other embodiments, intensity control (i.e., dimming) of one or more of the LEDs may be provided to further control the character of the composite light emitted from the multiple LEDs within the novel device.

The LEDs may be powered by self-contained batteries or from an external power source. In one implementation of a battery-powered device, each LCD may have an associated individual battery. In other implementations, all LEDs may be connected to and powered by a common battery.

It is believed that those of skill in the art will recognize the desirability of placing the one or more LCD light sources rearward from the suction tip so as to prevent blockage of light when the suction tip touches the tissues. Consequently, in alternate embodiments of the novel suction instrument, such rearward placement of the LCD light sources may be made.

The novel surgical suction instrument may be a single use, disposable device or, in alternate embodiments, the instrument may be a device intended for multiple uses and capable of withstanding sterilization.

It is, therefore, an object of the invention to provide a surgical suction instrument with a built-in illumination source.

It is another object of the invention to provide a surgical suction instrument with a built-in illumination source wherein the illumination is provided by at least two LEDs.

It is an additional object of the invention to provide a surgical suction instrument with a built-in illumination source wherein LEDs generating different wavelengths of light output may be selectively energized.

It is a further object of the invention to provide a surgical suction instrument with a built-in illumination source that may be powered by one or more self-contained batteries or may alternately be powered by an external power supply.

It is a still further object of the invention to provide a surgical suction instrument with a built-in illumination source that is provided as a single use instrument.

It is yet another object of the invention to provide a surgical suction instrument with a built-in illumination source that is adapted for reuse and that may be sterilized.

It is an additional object of the invention to provide a surgical suction instrument with a built-in illumination source wherein LEDs are disposed around a central suction passage.

It is a further object of the invention to provide a surgical suction instrument with a built-in illumination source wherein LEDs are disposed around a central suction passage and additional side suction channels are also provided.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 4a is a simplified electrical schematic block diagram of a first embodiment of an external power supply/controller for use with a surgical suction device of the invention;

FIG. 4b is a simplified electrical schematic block diagram of a second embodiment of an external power supply/controller for use with a surgical suction device of the invention.

DETAILED DESCRIPTION OF THE PREFERRED EMBODIMENT

The present invention provides a suctioning instrument fitted with an integral light source to optimize a surgeon's view of a surgical site. The addition of a light source capable of selectively generating a variety of colors further enhances selective visualization of specific tissue types and thereby enables better surgical technique.

The introduction of a surgical suctioning device with built-in lighting into the modern operating room environment is seamless as the new lighted surgical suction instrument merely replaces the prior art suction tips found in the majority of modern operating rooms. Consequently, no overhaul of either operating room equipment or operating room practice is required.

Figure 1:
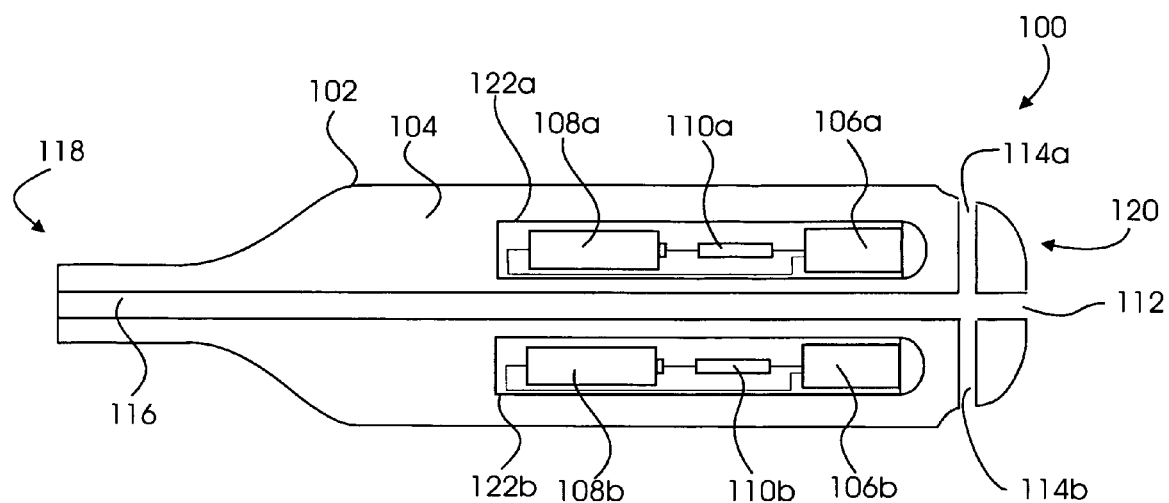
FIG. 1 is a side, elevational, cross-sectional, schematic view of one embodiment of a surgical suction device in accordance with the invention.
Figure 2:
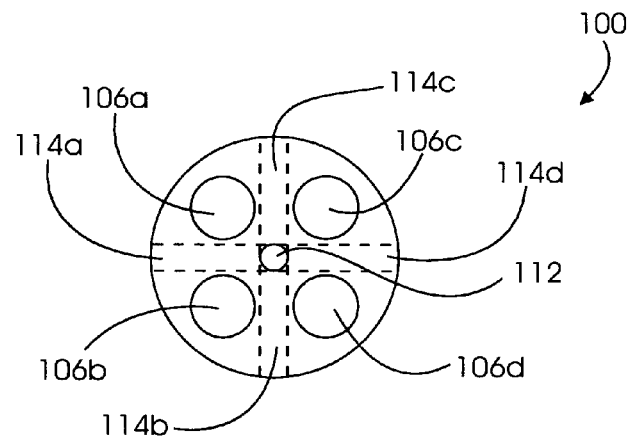
FIG. 2 is a front, elevational, schematic view of the surgical suction device of FIG. 1.

Referring first to FIGS. 1 and 2, there are shown side elevational, cross-sectional, schematic and front elevational, schematic views, respectively, of a first embodiment of the illuminating surgical suction instrument (SSI) in accordance with the invention, generally at reference number 100.

SSI 100 has a body 102 with a closed, transparent proximal end 120 and hollow interior region 104. Disposed within hollow interior region 104 of body 102 are four LED assembles 122a, 122b, 122c, 122d, each comprising a respective LED 106a, 106b, 106c, 106d, a respective associated power supply, shown schematically at reference numbers 108a . . . 108d. Typically power supplies 108a . . . 108d consists of a battery but it will be recognized that other devices, not shown, may be substituted therefore.

Switches 110a . . . 110d, disposed between respective ones of power supplies 108a . . . 108d and LEDs 106a . . . 106d selectively control each of associated LEDs 106a, 106b, 106c, 106d, are disposed within respective LED assemblies 122a . . . 122d.

While four LEDs 106a, 106b, 106c, 106d have been chosen for purposes of disclosure, it will be recognized that other numbers of LEDs may be chosen to meet a particular operating circumstance or environment. It will be further recognized that in order to selectively provide light of different wavelengths, at least two LEDs must be provided. Light provided at different wavelengths (i.e., colors) may aid the surgical team in identifying or highlighting certain tissue types. For example, muscle tissue is typically red while connective tissue is typically whitish or cream colored. Venous blood is dark purplish red while arterial blood is light orangish red. Adipose (fat) is typically yellow. A particular tissue or anatomical feature may be highlighted by illuminating it with a contrasting color light. For example, green light highlights red muscle tissue, blue light highlights fatty tissue, etc.

In other instances, particular chemicals may be instilled into a particular tissue or organ to highlight certain cells. In one example, the chemical hexyl aminolevulinate (HAL) may be instilled into a bladder as part of a cystoscopic procedure. Cancerous cells then appear red when illuminated with blue light. The SSI 100 of the invention may be used to selectively illuminate cells with selected wavelengths of light during a surgical procedure.

There are many commercially available LEDs known to those of skill in the art. For example, a GaAs/GaP LED emits light having a wavelength of 635 nm (red); an InGaAIP LED emits light at 592 nm (yellow); a Gap LED emits light at a wavelength of 555 nm (green); and a SiC/GaN LED emits light having a wavelength of 470 nm (blue). These examples are not inclusive and many other LEDs may be chosen to implement the SSI of the invention. Consequently, the invention is not considered limited to any particular combinations of LEDs emitting particular light wavelengths. Rather, the invention includes LEDs generating light at any wavelength.

In the embodiment chosen for purposes of disclosure, an LED generating white light as well as additional LEDs generating light wavelengths of 592 nm (yellow), 555 nm (green), and 470 nm (blue) have been chosen. It will be recognized that LEDS 106a . . . 106d may be chosen to provide particular wavelengths of light necessary to meet a particular operating circumstance or environment. Consequently, the invention is not considered limited to a particular choice of the wavelengths of LEDs 106a . . . 106d. Rather, the invention comprehends any selection of light wavelengths for LEDs 106a . . . 106d.

Switches 110a . . . 110d are disposed for local actuation by the surgeon or another member of the surgical team, or, as discussed in more detail hereinbelow, switches 164a . . . 164d (FIGS. 4a, 4b, 4c) that may be located remote from SSI 100. One possible type of switch 110a . . . 110d that may be sealed within power supplies 108a . . . 108d is a magnetically actuated, toggling reed switch, not shown. Such reed switches may be externally activated or deactivated using a small, external magnet, not shown. Such latching magnetic switches, actuating magnets therefor, other types of switches that may be substituted therefor are believed to be well known to those of skill in the art may also be used to selectively control LEDs 106a . . . 106d.

LEDs 106a, 106b, 106c, 106d are axially disposed around a central suction channel 112. Optionally, additional side suction channels 114a . . . 114d may be interspersed between adjacent ones of LEDs 106a . . . 106d.

Central suction channel 112 and optional side suction channels 114a . . . 114d extend longitudinally along and within body 102 and terminate at suction inlet 116 disposed at a distal end 118 of body 102. Suction inlet 116 is sized and configured for removable interconnection with a standard suction conduit, not shown. It will be recognized that suction inlet 116 may be equipped with a connection fitting, not shown, to facilitate removable interconnection with a standard suction conduit. Such fittings are believed to be well known to those of skill in the art and are, therefore, not further discussed herein.

In alternate embodiments of surgical suction instrument 100, power supplies 108a . . . 108d may be combined into a single, higher capacity battery located in a suction handle, not shown, to which SSI 100 may be connected. In still other alternate embodiments, switches 110a . . . 110d may also be located in the suction handle.

Figure 3:
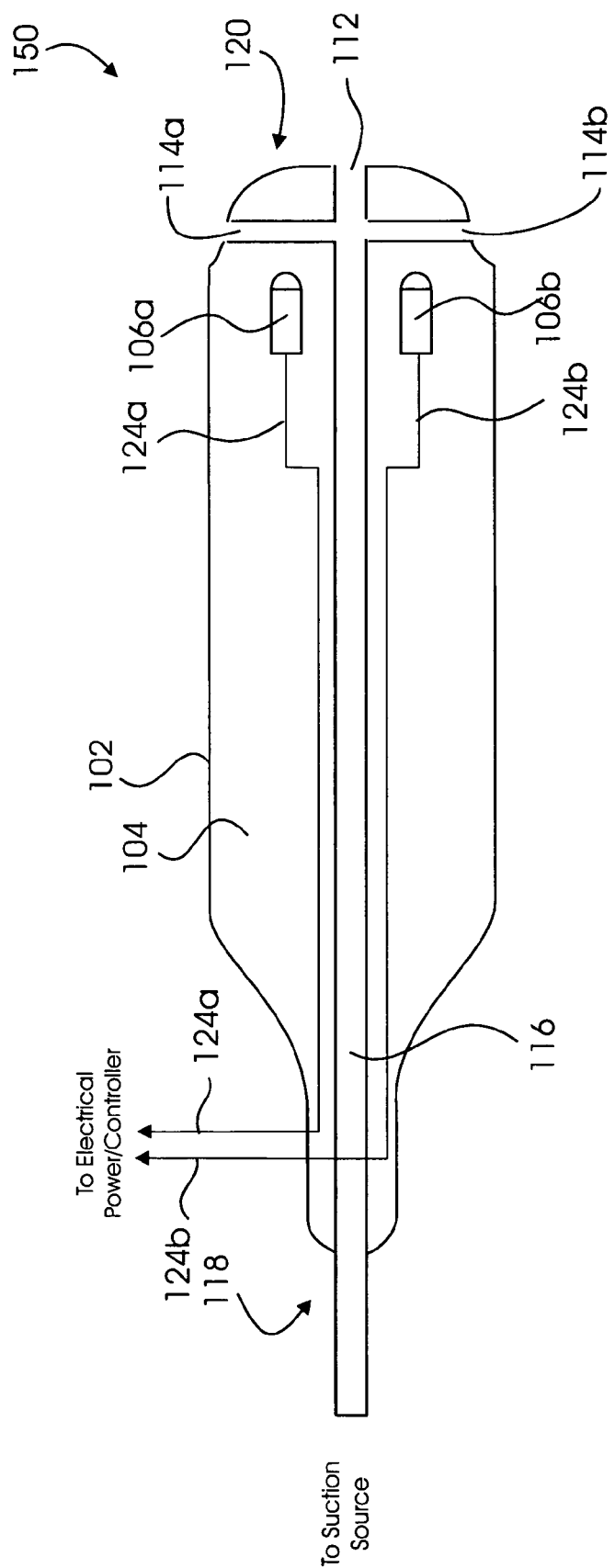
FIG. 3 is a side, elevational, cross-sectional, schematic view of an alternate embodiment of a surgical suction device in accordance with the invention.

Referring now to FIG. 3, there is shown a side, elevational, cross-sectional schematic view of an alternate embodiment of the surgical suction instrument (SSI) of the invention, generally at reference number 150. In SSI 150, LED assemblies 122a . . . 122d have been eliminated and only LED's 106a . . . 106d remain in interior region 104 of body 102. Each LED 106a . . . 106d is electrically connected to an external power source/controller 160 (FIG. 4a), 170 (FIG. 4b), or 180 (FIG. 4c via associated electrical conductor 124a . . . 124d.

Electrical conductors 124a . . . 124d typically extend rearward from respective LEDs 106a . . . 106d along central suction channel 112 and then along an outside surface of suction inlet 116.

Electrical conductors 124a . . . 124d exit body 102 and then may be extended to connect to a power supply/controller 160, 170, or 180 as desired.

Referring now also to FIG. 4a there is shown a simplified electrical schematic block diagram of a first embodiment of an external power supply/controller, generally at reference number 160. Power supply/controller 160 contains a battery 162 or other similar power source that allows operation of SSI 150 in isolation from an external power source such as the AC mains. Battery 162 may be either a non-rechargeable or a rechargeable battery. If battery 162 is rechargeable, a battery charger, not shown, may be built into power supply/controller 160. Such battery chargers are believed to be well known to those of skill in the art and, consequently, are not further described herein.

Battery 162 is connected to four switches 164a . . . 164d that functionally replace corresponding switches 110a . . . 110d of SSI 100 of FIG. 1. Unlike switches 110a . . . 110b that needed to be both small and externally actuateable while sealed within body 102 of SSI 100, switches 164a . . . 164d may be of any type of switch suitable for use in an operating room environment.

Each switch 162a . . . 162d controls the flow of electrical energy to a respective LED 106a . . . 106d located within body 102 of SSI 150 and connected thereto by respective electrical conductors 124a . . . 124d.

It will be recognized that it may be desirable to have a connector, not shown, between power supply/controller 160 and SSI 150. Such connectors are also believed to be well known to those of skill in the art and any suitable connector may be utilized. Consequently, the invention is not considered limited to a configuration either with or without a connector or to any specific connector type if one is present.

Referring now also to FIG. 4b, there is shown an alternate embodiment of a power supply/controller, generally at reference number 170. Power supply/controllers 170 is adapted for connection to an external source of electrical power, typically to an electrical outlet, not shown, connected to the AC mains.

In power supply/controller 170, battery 162 is replaced by a power supply 172. Such power supplies 172 typically contain a step-down transformer, a rectifier, and a ripple filter typically consisting of one or more filter capacitors, none of which are specifically identified. Such power supplies 172 are believed to be well known to those of skill the art and, consequently, are not further described herein. Any suitable circuit arrangement and/or power supply components may be used to provide electrical energy at an appropriate voltage and at a sufficient current to LEDs 106a . . . 106d. Strict electrical codes typically apply to electrical equipment for use in an operating room and similar medical environments. It is assumed that all devices used in implementing SSIs 100, 150 and/or power supply controllers 160, 170, 180 (FIG. 4c) meet all necessary national, state, and local codes for such equipment.

A main power switch 174 is connected between the AC mains and power supply 172.

Figure 4C:
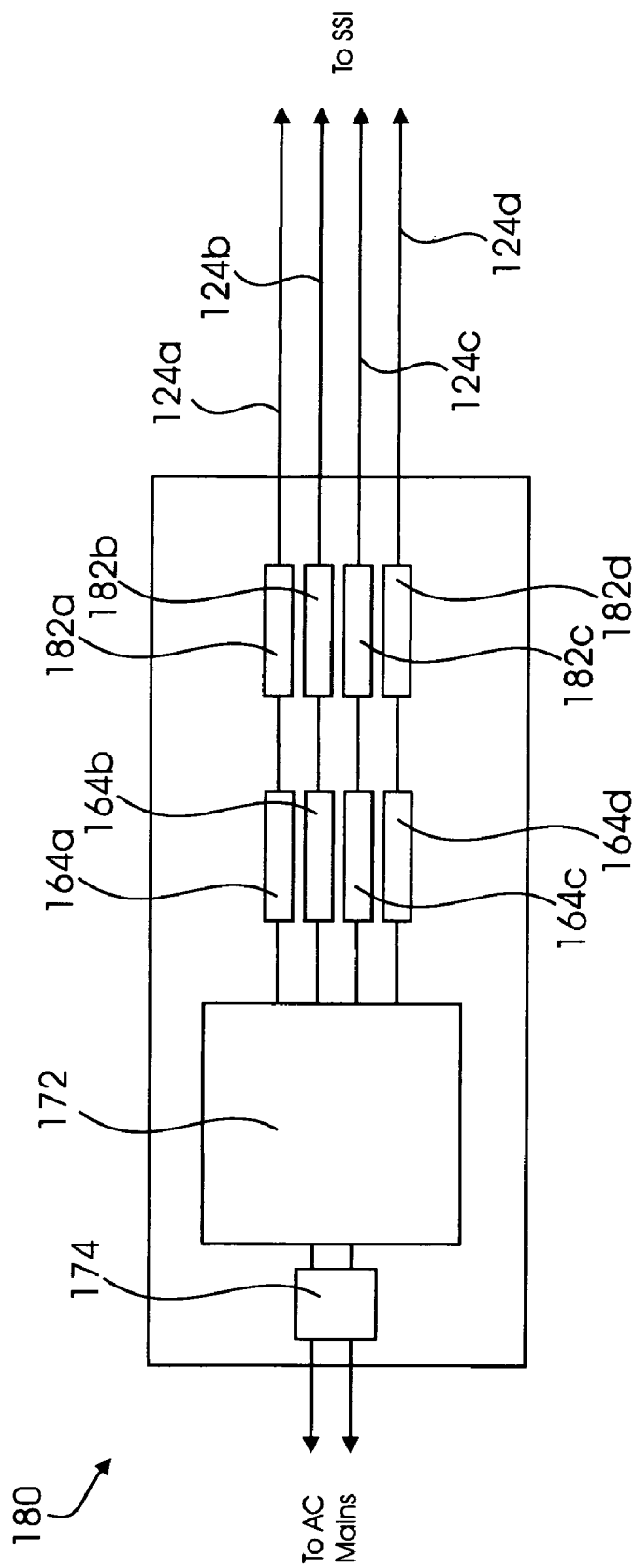
FIG. 4c is a simplified electrical schematic block diagram of a third embodiment of an external power supply/controller for use with a surgical suction device of the invention.

Referring now also to FIG. 4c, there is shown yet another embodiment of a power supply/controller, generally at reference number 180. The only substantial difference between power supply/controllers 170 and 180 is the inclusion of variable controls 182a . . . 182d included in series with switches 164a . . . 164d in the later. Variable controls 182a . . . 182d are provided to vary the light output of respective LEDs 106a . . . 106d. Variable controls 182a . . . 182d may be implemented in a number of ways all considered to be well known to those of skill in the electrical control arts. For example, variable controls 182a . . . 182d may be a simple potentiometer or a sophisticated electronic circuit to control the voltage and/or current supplied to a respective one of LEDs 106a . . . 106d. The ability to control the intensity of one or more of LEDs 106a . . . 106d provides the surgeon with more options for providing optimized illumination to the surgical site for a particular procedure.

As light from LEDs 106a . . . 106d may be blocked when transparent proximal end 120 of body 102 contacts tissue, it will be recognized that LEDs 106a . . . 106d could be reoriented such that such light blockage is avoided. Consequently, the invention is intended to cover such orientations of LEDs 106a . . . 106d.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A surgical suction instrument, comprising:
   a) an elongated tubular body having a smooth, closed, transparent, proximal end, a distal end, and a hollow interior;
   b) a central suction channel centrally disposed within said hollow interior and substantially parallel to a major axis of said body, said central suction channel having an open proximal end penetrating said smooth, closed, transparent, proximal end of said body and communicative with a space outside said smooth, closed, transparent, proximal end, and an open distal end proximate said distal end of said body;

c) at least one LED assembly disposed axially around and parallel to said central suction channel proximate said proximal end thereof, each of said at least one LED assemblies comprising an LED for generating light of a respective, predetermined wavelength and projecting said generated light forward through said smooth, closed, transparent, proximal end of said body; and d) at least two side suction channels axially disposed around said central suction channel and interspersed between adjacent ones of said at least one LED assembly, each having an open, proximal end proximate said smooth, closed, transparent, proximal end of said body, each of said at least two side suction channels being communicative with a space surrounding said body and, at a respective distal end thereof, with said central suction channel.

2. The surgical suction instrument as recited in claim 1, wherein at least one of said at least one LED assembly generating light of a respective, predetermined wavelength generates polychromatic white light.

3. The surgical suction instrument as recited in claim 1, wherein said at least one LED assembly comprises four LED assemblies, each of said four LED assemblies generating light of a color selected from the group: white, yellow, green, blue, and red.

4. The surgical suction instrument as recited in claim 2, wherein each of said at least one LED assembly further comprises:
   i) an LED for generating light of a predetermined wavelength; and
   ii) a power source operatively connected to said LED.

5. The surgical suction instrument as recited in claim 4, wherein each of said LED assemblies further comprises:
   ii) a switch operatively connected between said power source and said LED.

6. The surgical suction instrument as recited in claim 5, wherein said switch is actuatable from outside said body.

7. The surgical suction instrument as recited in claim 2, further comprising:
   d) a power supply/controller disposed externally to said body of said surgical suction instrument and operatively connected to said at least one LED disposed therein, said power supply/controller comprising:
   i) a power source; and
   ii) an electrical conductor disposed between said power source and at least one of said at least one LED disposed in said body of said surgical suction instrument.

8. The surgical suction instrument as recited in claim 7, wherein said power supply/controller further comprises:
   iii) at least one switch operatively connected between said power source and said electrical conductor.

9. The surgical suction instrument as recited in claim 7, wherein said power source comprises at least one selected from the group: a non-rechargeable battery, a rechargeable battery, and a power supply connected to AC mains.

10. The surgical suction instrument as recited in claim 7, further comprising:
   e) means for variably controlling at least one selected from the group: a voltage, and a current supplied to at least one of said at least one LEDs disposed between said power source and said at least one of said at least one LED;
   whereby generated light intensity of said at least one of said at least one LED may be varied.

* * * * *